United States Patent [19]
Brown et al.

[11] Patent Number: 5,121,836
[45] Date of Patent: Jun. 16, 1992

[54] RETAINER FOR COMBINED SURGICAL SUTURE-NEEDLE DEVICE

[75] Inventors: David L. Brown, Wallingford; Henry A. Holzwarth, Weston, both of Conn.

[73] Assignee: United States Surgical Corporation, Norwalk, Conn.

[21] Appl. No.: 826,235

[22] Filed: Jan. 23, 1992

Related U.S. Application Data

[63] Continuation of Ser. No. 529,222, May 25, 1990, abandoned, which is a continuation-in-part of Ser. No. 388,152, Aug. 1, 1989.

[51] Int. Cl.⁵ .............................. A61B 17/04
[52] U.S. Cl. .................... 206/63.3; 206/438
[58] Field of Search .......... 206/63.3, 388, 380, 206/227, 438, 476

[56] References Cited

U.S. PATENT DOCUMENTS

| | | |
|---|---|---|
| 3,162,307 | 12/1964 | Regan, Jr. . |
| 3,857,484 | 12/1974 | Thyen .................. 206/63.3 X |
| 3,939,969 | 2/1976 | Miller et al. ............. 206/63.3 |
| 3,951,261 | 4/1976 | Mandel et al. ............ 206/227 |
| 3,985,227 | 10/1976 | Thyen et al. ............ 206/63.3 |
| 4,063,638 | 12/1977 | Marwood ............... 206/63.3 |
| 4,089,409 | 5/1978 | Cerwin .................. 206/63.3 |
| 4,120,395 | 10/1978 | Mandel et al. ........... 206/63.3 |
| 4,249,656 | 2/1981 | Cerwin et al. ........... 206/63.3 |
| 4,253,563 | 3/1981 | Komarnycky ........... 206/63.3 |
| 4,406,363 | 9/1983 | Aday ................... 206/63.3 |
| 4,412,614 | 11/1983 | Ivanov et al. ........... 206/63.3 |
| 4,413,727 | 11/1983 | Cerwin et al. . |
| 4,496,045 | 1/1985 | Ferguson et al. ......... 206/63.3 |
| 4,533,041 | 8/1985 | Aday et al. . |
| 4,574,948 | 3/1986 | Huck et al. . |
| 4,574,957 | 3/1986 | Stead . |
| 4,615,435 | 10/1986 | Alpern et al. . |
| 4,708,241 | 11/1987 | Black . |
| 4,884,681 | 12/1989 | Roshdy et al. ........... 206/63.3 |

FOREIGN PATENT DOCUMENTS

0046518 3/1982 European Pat. Off. .
0276964 8/1988 European Pat. Off. .

Primary Examiner—Paul T. Sewell
Assistant Examiner—Jacob K. Ackun, Jr.
Attorney, Agent, or Firm—Peter G. Dilworth; Rocco S. Barrese; Thomas R. Bremer

[57] ABSTRACT

A multi-panel suture retainer provides ready access to, and removal of, a quantity of stored combined surgical needle-suture devices.

24 Claims, 5 Drawing Sheets

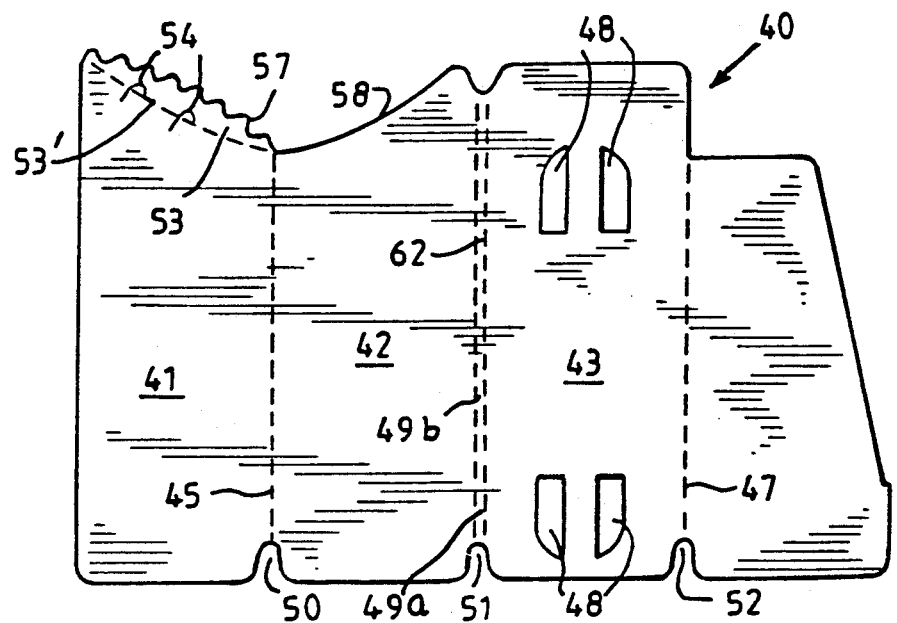
_Fig. 3_
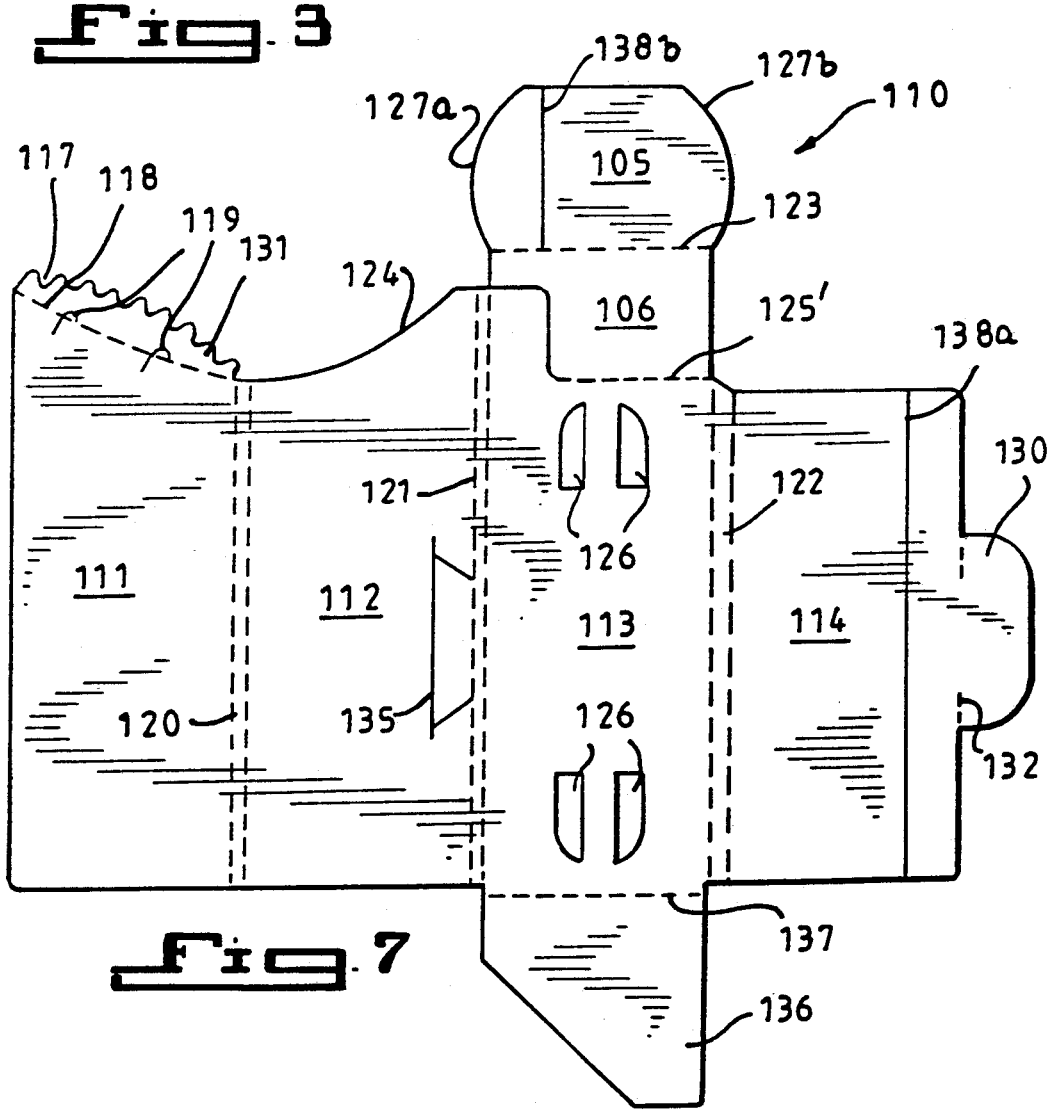
_Fig. 7_

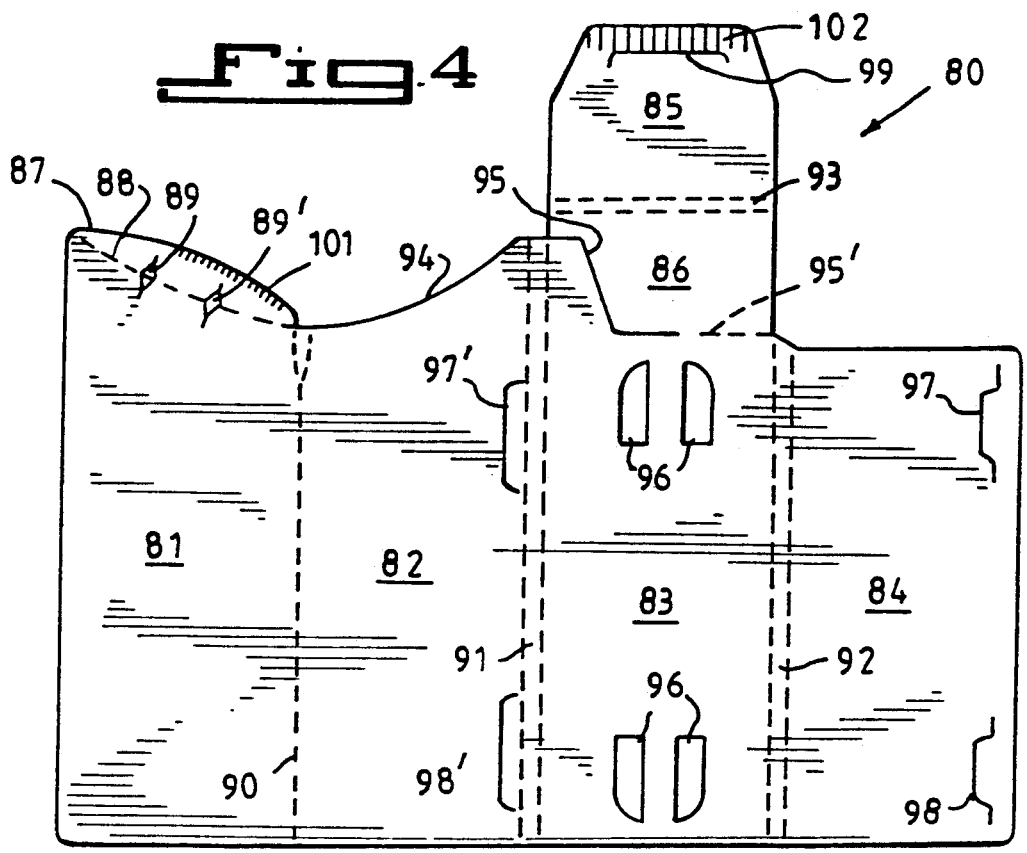
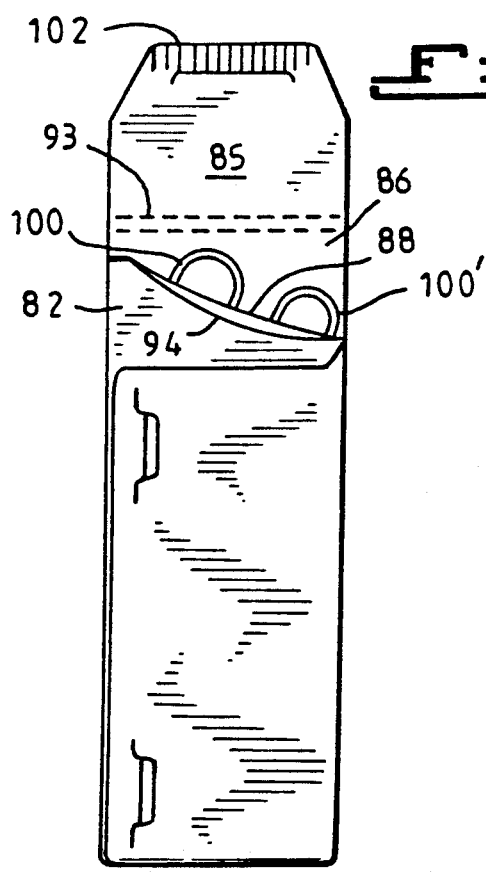
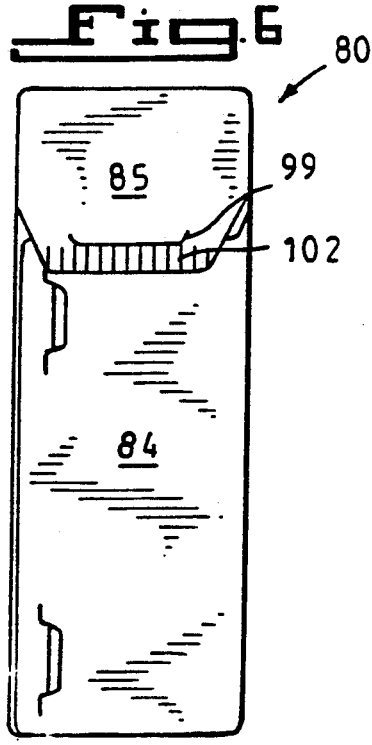

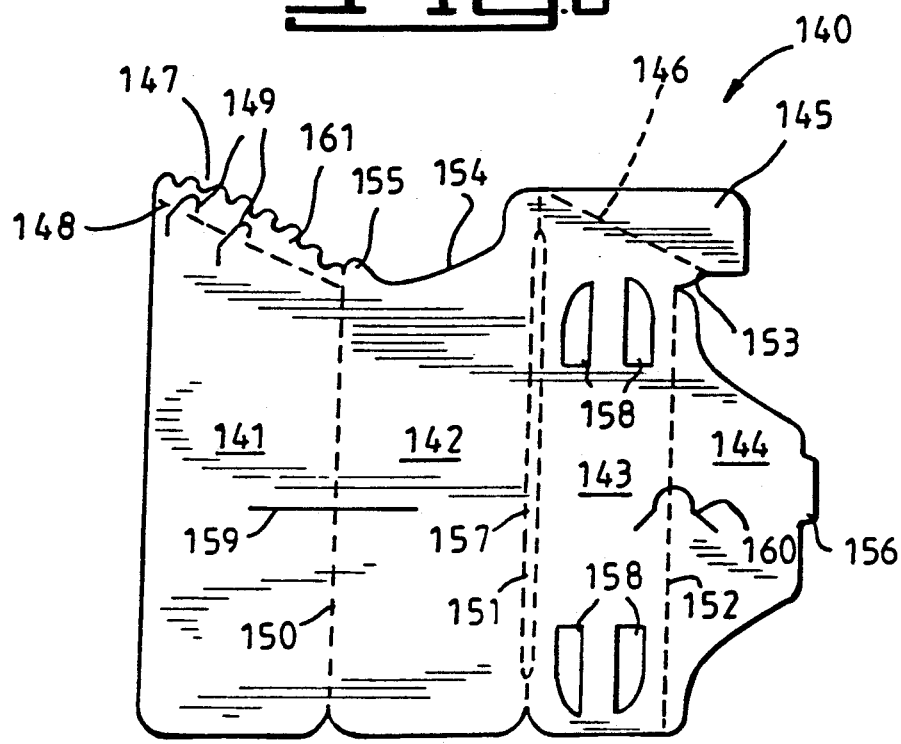
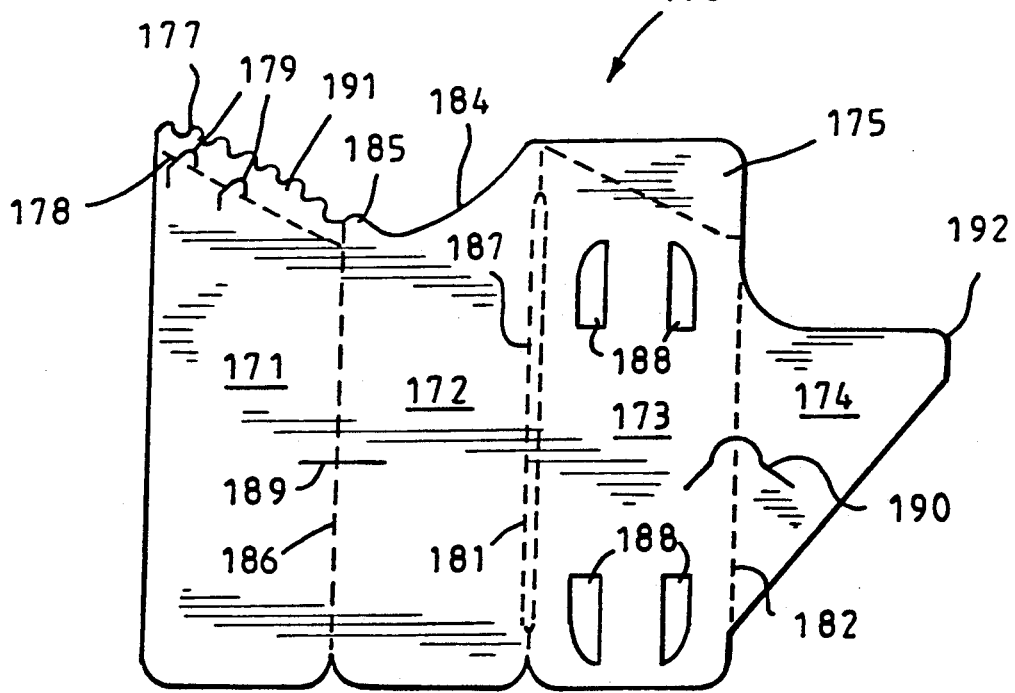

RETAINER FOR COMBINED SURGICAL SUTURE-NEEDLE DEVICE

CROSS REFERENCE TO RELATED APPLICATION

This is a continuation-in-part of commonly assigned, copending U.S. patent application Ser. No. 388,152, filed Aug. 1, 1989.

BACKGROUND OF THE INVENTION

This invention relates to a retainer for a combined surgical needle-suture device, also commonly referred to as an "armed suture" or merely a "suture", as part of a suture package. Retainers for sutures are known, inter alia, from U.S. Pat. Nos. 3,857,484; 3,939,969; 3,951,261; 3,985,227; 4,063,638; 4,089,409; 4,120,395; 4,192,420; 4,249,656; 4,427,109; 4,253,563; 4,406,363; 4,412,614; 4,483,437; 4,491,218; 4,555,016; 4,572,363; 4,574,948; 4,574,957; 4,615,435; 4,708,241 and 4,813,537.

As an essential component of a suture package, the suture retainer should possess good storing qualities, provide safety in handling and permit ready access to, and removal of, the stored sutures

SUMMARY OF THE INVENTION

By way of meeting the foregoing criteria, there is provided in accordance with this invention, an armed suture retainer comprising four interconnected panels, namely, a needle retaining panel, a front cover panel connected to the needle retaining panel, a suture winding panel connected to the front cover panel and a fold-over panel connected to the suture winding panel.

The foregoing suture retainer possesses several advantages over known types of retainers, e.g., as described in U.S. Pat. No. 4,249,656 referred to supra, the contents of which are incorporated by reference herein. A particularly important advantage of the suture retainer herein lies in the relative ease with which operating room personnel are able to view the needles and grasp them with forceps to effect their removal. These capabilities are made possible by the configurations of the first and second panels which, in the fully folded retainer, permit a highly visible needle display section from which each needle in the retainer can be easily removed.

BRIEF DESCRIPTION OF THE DRAWINGS

FIG. 3 is a plan view of another embodiment of an armed suture retainer in accordance with this invention shown in the fully unfolded condition;

FIGS. 4, 5 and 6 are plan views of another embodiment of the armed suture retainer herein also shown in the fully unfolded, partially folded and fully folded conditions, respectively; and, FIGS. 7-10 are plan views of still other embodiments of an armed suture retainer in accordance with this invention shown in the fully unfolded condition.

DESCRIPTION OF THE PREFERRED EMBODIMENTS

Figure 1:
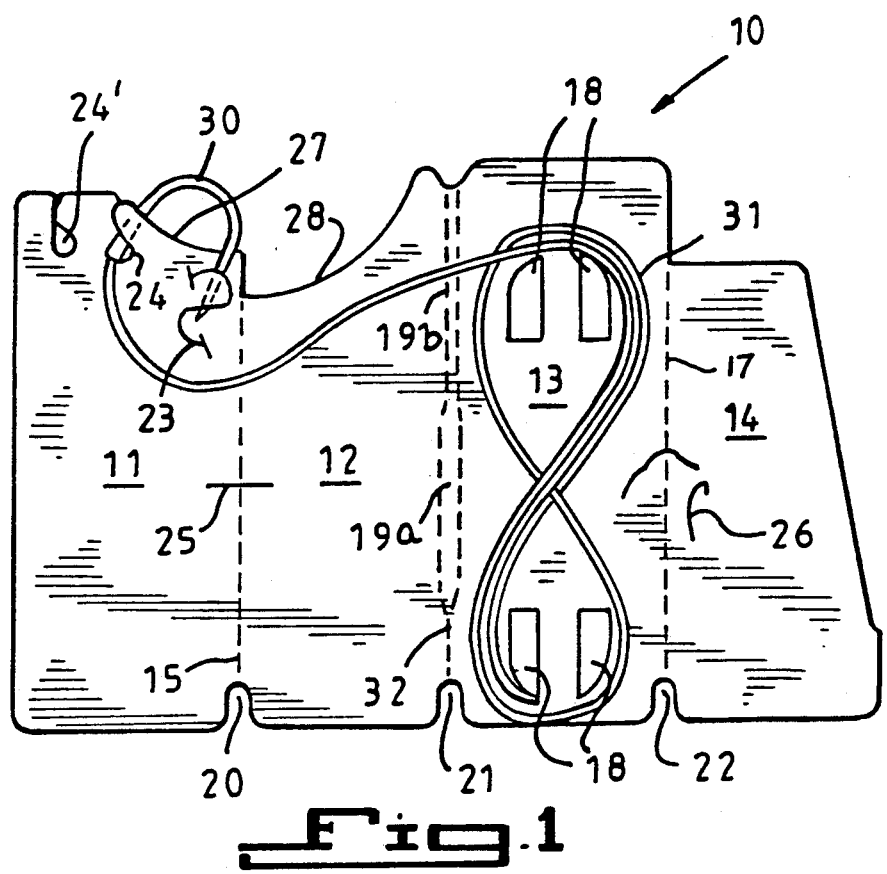
FIG. 1 is a plan view of one embodiment of an armed suture retainer in accordance with this invention loaded with a combined surgical needle-suture device and shown in the open condition.
Figure 2:
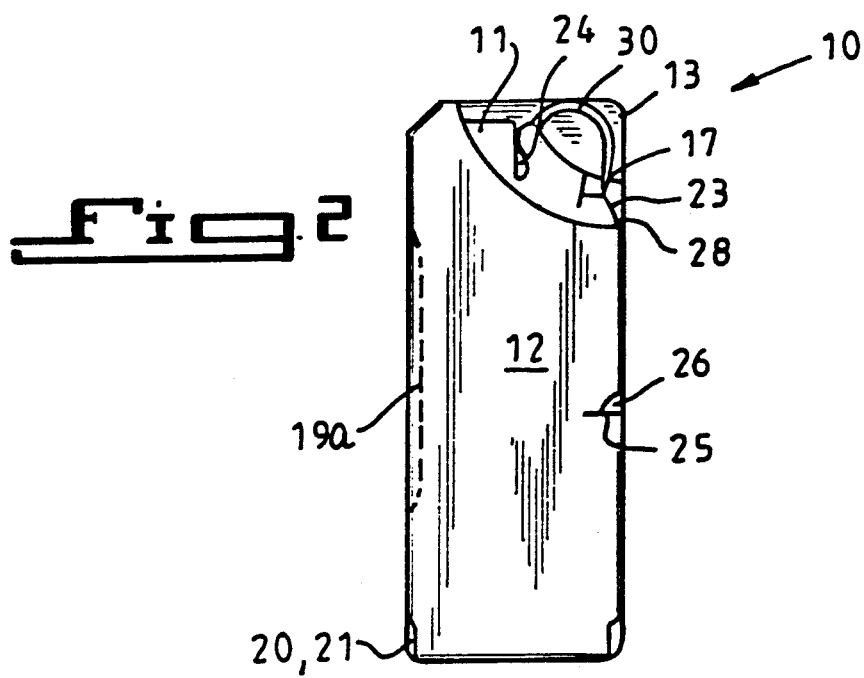
FIG. 2 is a plan view of the armed suture retainer of FIG. 1 shown in the fully folded condition.

FIG. 1 illustrates a fully unfolded armed suture retainer 10 in accordance with this invention and FIG. 2 illustrates retainer 10 in the fully folded condition which it assumes when received within the pocket of an outer suture package, e.g., as described in copending parent U.S. patent application Ser. No. 388,152, filed Aug. 1, 1989.

Retainer 10 is provided as a series of four interconnected panels, namely, needle retainer panel 11 possessing an upper sloping edge 27, front cover panel 12 which also possesses an upper sloping edge 28, suture winding panel 13 (which also functions as the rear panel of the fully folded retainer) and fold-over panel 14. Retainer 10 is preferably formed from a single sheet of suitable material, e.g., stiff paper or paperboard such as 5 point to 12 point solid, Tyvek, bleached sulfate board, plastics, foils, laminates, and the like, which is die cut to provide the desired configuration. The panels are joined to each other along perforate, or score, lines 15, 32 (and its associated gusset sections 19a and 19b) and 17. Central gusset sections 19a and 19b accommodate a limited degree of expansion of the retainer in its loaded, fully folded condition. Other gusset configurations can also be employed for this purpose, e.g., a continuous pair of parallel fold lines or perforations which provide a narrow expansion section (line 49a and 49b defining gusset 62 in the retainer of FIG. 3).

In the fully folded condition of the retainer and as shown in FIG. 2, a portion of needle 30 is readily visible in the upper section of the retainer and is easily gripped by forceps for removal. Die cut 25 cooperates with die cut 26 to provide a snap-lock feature which maintains the retainer in the fully folded condition. Rounded indentations 20, 21 and 22 serve to prevent the suture from becoming caught between the panels when folded.

To load needle component 30 with its attached suture component 31 into retainer 10, the retainer is first mounted on a winding fixture by means of loading pins (not shown) which project through openings 18 in panel 13. The point of needle 30 is then inserted in die cut 23 which is shaped somewhat like a reversed "S" by threading the point under the upper and the lower half of the reversed "S" cut. Slight tension is maintained on suture 31 from this stage of the loading procedure to its conclusion to ensure that needle 30 will maintain its placement in die cut 23 as previously described. The shank of needle 30 is then threaded through one of teardrop-shaped cutouts 24 or 24', cutout 24 being used for smaller needles (as shown in FIG. 2) and cutout 24' being used for larger needles. After panel 11 has been folded over onto panel 12, suture 31 is wound in a figure "8" pattern around the loading pins projecting through openings 18 in panel 13. Retainer 10, now loaded with needle 30 and attached suture 31, is released from the loading pins, panel 14 is folded over on panel 13 and the partly folded-over structure is given a final folding along perforate line 32 and gussets 19a and 19b. Finally, a slight counter-directional movement of the upper section of the retainer against its lower section sets the aforementioned snap-lock in place providing the fully assembled, loaded retainer of FIG. 2.

Referring to FIG. 3, there is illustrated another embodiment of the armed suture retainer of the present invention. Retainer 40 is provided as a series of four interconnected panels, namely, needle retainer panel 41 possessing an elliptical flap 53 defined by an arcuately shaped perforated fold line 53', front cover panel 42 possessing upper sloping edge 58, suture winding panel 43 which also functions as the rear panel of the fully folded retainer, and fold over panel 44. Needle retainer panel 41 possesses an arcuately serrated edge 57 of sinusoidal pattern configured to retain surgical needles thereon. The serrated edge 57 replaces cut-outs 24 and 24' and die cut 23 of the embodiment of FIG. 1 and provides an alternative means for needle retention.

Again, referring to FIG. 3, a pair of inverted "J-cuts" 54 are located in spaced relation along arcuate score line 53'. When elliptical panel 53 is folded downward along the arcuate score line 53', the "J-cuts" 54 provide two parabolic openings in the elliptical panel. These openings permit sterilizing gas to readily enter the retainer in its fully folded condition. Additionally, when elliptical panel 53 is folded downward, "J-cuts" 54 provide two parabolic fingers extending upwardly and coplanar with needle retainer panel 41. These fingers provide "saddles" against or around which the needle shank and attached suture may be positioned. Panels 42 and 43 are joined together by parallel score lines 49a and 49b, to provide central gusset section 62.

Once the needles are secured within or against a sinusoidal curve of arcuately serrated edge 57 of elliptical flap 53, the latter is folded over at arcuate edge 53'. The arcuate shape of 53' prevents extension panel 53 from folding flat against retaining panel 41. When needle retaining panel 41 is folded over at perforate score 45 upon front cover panel 42, flap 53 serves to space needle retaining panel 41 from front cover panel 42, thereby greatly improving the visibility and accessibility of needle components. In this position, the needles are securely retained by engagement with serrations 57 of flap 53 and front cover panel 42.

Referring to the embodiment of armed suture retainer 80 of FIGS. 4–6, needle retaining panel 81 is connected to needle protecting panel 82 through single perforate score 90, panel 82 being connected to suture winding panel 83 (which is also the rear panel of the fully folded retainer) through double perforate score 91, panel 83 being connected to fold-over panel 84 through double perforate score 92. Diamond-shaped cutouts 89 and 89' are provided along upper sloping edge 88 of panel 81 in the region receiving needle components 100 and 100' (FIG. 5) of two surgical suture-needle devices. Once the needles are secured within serrations 101 of extension panel 87, the latter folds over sloping edge 88 to provide additional protection for the needles. With the needles in place and extension panel 87 folded over, needle retaining panel 81 is folded over at perforate score 90 upon needle protecting panel 82 and the surgical suture components of the combined suture-needle devices (not shown) are wound in a figure "8" pattern upon suture winding panel 83 with the aid of loading pins projecting through openings 96 in much the same manner as previously described in connection with the suture retainer embodiment of FIGS. 1 and 2. Combined overlying panels 81 and 82 are thereafter folded over at double perforate score 91 upon suture winding panel 83 to slightly compress the wound sutures and retain them in place on panel 83. Panel 84 is then folded over at double perforate score 92 upon the reverse side of panel 82, die-cut locking tabs 97 and 98 on panel 84 cooperating with die-cut locking slots 97' and 98' on panel 82 to provide the nearly fully folded retainer shown in FIG. 5. Finally, outer extension panel 85 is folded over at double perforate score 93 upon both inner extension panel 86 and exposed needles 100 and 100' with die-cut tab locking 99 on panel 85 engaging the upper edge of fold-over panel 84 to provide the fully folded suture retainer shown in FIG. 6. The lower edge of inner extension panel 86 is advantageously provided with a die-cut separation line 95 and perforate score line 95' which allows the entire combined extension panel 85, 86 to be conveniently separated from panel 83 or folded back upon itself thus permitting access to needles 100 and 100' from the reverse side of retainer 80 as well as from its front side. Even when combined extension 85, 86 is not separated from panel 83, the combined extension may be folded back along separation line 94 and perforate score 95' to provide needle visibility and accessibility from the rear of retainer 80. Outer extension panel 85 possesses a knurled section 102 which facilitates the opening of fully closed retainer 80 by providing a surface for easy engagement of the lower section of extension panel 85.

Referring to FIG. 7, illustrating still another embodiment of the suture retainer of the present invention, retainer 110 features four panels, namely, needle retaining panel 111, needle protecting panel 112, suture winding panel 113 and fold-over panel 114. Double perforated scores 120 and 121 define gussets which allow for expansion of the loaded retainer in its closed condition.

Raised ribs 138a and 138b project outwards from the reverse sides of fold over panel 114 and extension panel 105, respectively. When retainer 110 is in the closed position, raised ribs 138a provide a slight concave bend to fold-over panel 114, which enables panel 114 to resist any tendency to thrust away from needle retainer panel 111.

Needle protection panel 112 possesses a trapezoidal shaped locking slit 135. When retainer 110 is in the fully closed position, locking tab 130 folds back at a 180° angle upon its score line 132 and cooperates with closing slit 135 of panel 112 to provide a completely secured retainer.

Along the lower edge of the suture winding panel 113 is a triangular extension panel 136 connected to winding panel 113 by single perforate score line 137. Triangular panel 136 folds over upon perforate score line 137 and secures a suture thread to retainer panel 113.

Extension panel 105 possesses convex sides 127a and 127b which facilitate the opening of retainer 110 by operating room personnel. When retainer member 110 is in a fully closed position, convex sides 127a and 127b extend outwards from the sides of retainer member 110 and provide two areas for easy engagement of extension panel 105.

Needle retaining panel 111 possesses a sinusoidal serration configuration 117 and a pair of "J" cuts 119 similar in design and function to the corresponding configurations of retainer 40 of FIG. 3.

Referring to FIG. 8, there is illustrated yet another embodiment of the present invention. Retainer 140 features four panels, namely, needle retaining panel 141, front cover panel 142, suture winding panel 143, and fold-over panel 144. Double perforated scores 151 define a gusset which allows for expansion of the loaded retainer in its closed condition. Front cover panel 142 possesses an upper sloping edge 154 which slopes upward to form a rounded projection 155.

Suture winding panel 143 is significantly narrower than the suture winding panels of other embodiments described herein. The narrower panel facilitates winding of the suture and minimizes the possibility that suture loops may become entangled. Suture winding panel 143 possesses triangular shaped extension panel 145 which folds over along perforated score line 146 to provide a needle protection flap in the loaded and closed condition of the retainer card. When panel 143 is folded over onto panel 142, slit 153 can be made to engage rounded projection 155 thus locking the two panels together. Bell-shaped fold-over panel 144 possesses a tab 156 which cooperates with slit 157 to secure a wound suture upon suture winding panel 143. Die cut 159 cooperates with die cut 160 to provide a snap-lock feature which maintains the retainer in the fully closed condition.

Referring to FIG. 9, illustrating still another embodiment of the suture retainer of the present invention, retainer 170 possesses four panels, namely, needle-retainer panel 171, front cover panel 172, suture-winding panel 173 and fold-over panel 174. The openings 188 of suture winding panel 173 which receive the loaded pins are positioned further apart than in previous embodiments. This positioning reduces the likelihood of suture entanglement since the freedom of movement of the wound suture is limited to one direction (i.e., inwardly). In addition, loop positioning will be better achieved and secured by compression of adjoining panels more closely adjacent the fold-lines. Triangular fold-over panel 174 possesses outer edge 192 which, in the folded condition of the retainer, interlocks with slit 187 to secure the wound suture to suture winding panel 173.

Figure 10:
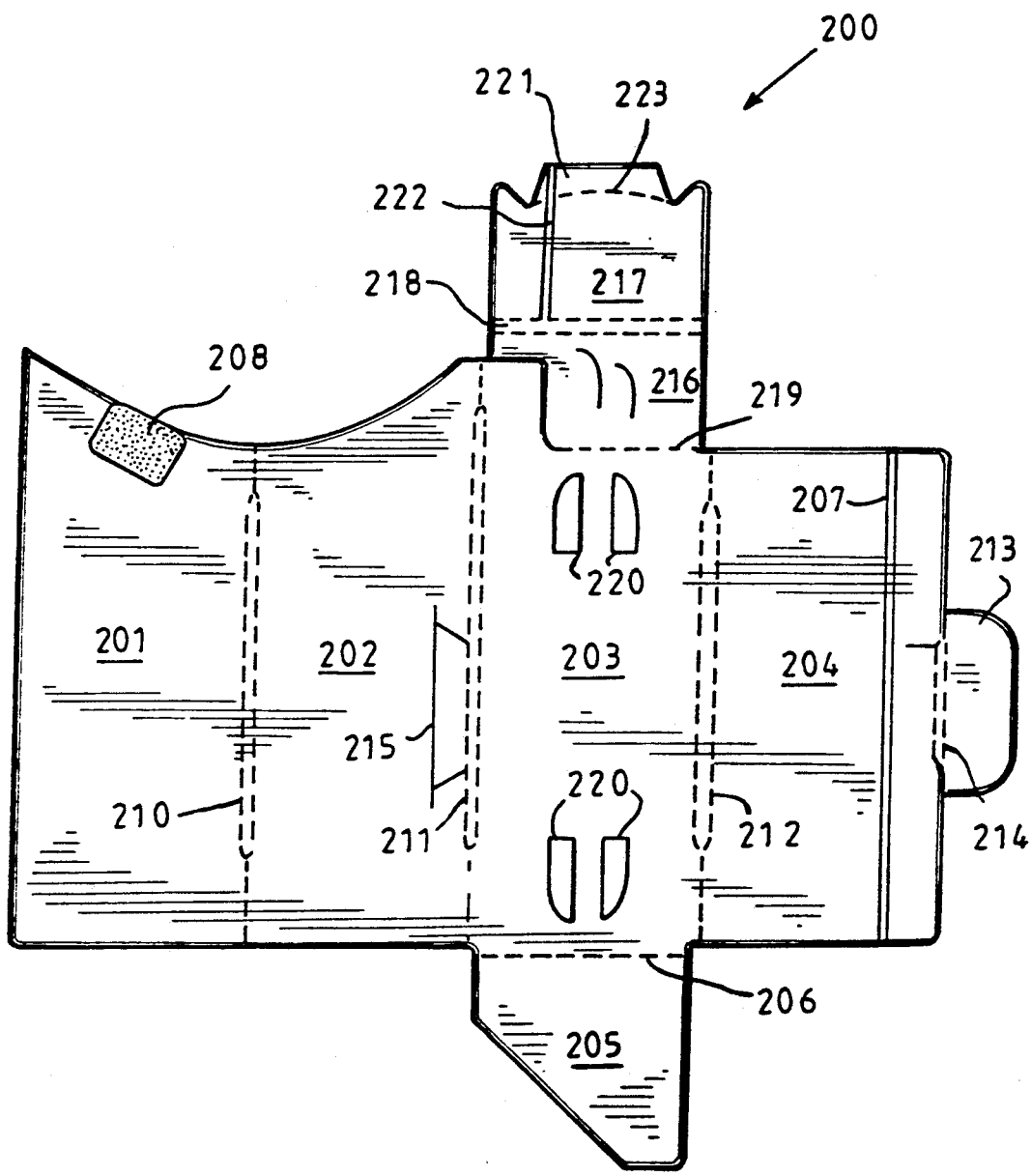

Referring to FIG. 10 illustrating still another embodiment of the present invention, retainer 200 possesses four panels, namely, needle retainer panel 201, front cover panel 202, suture winding panel 203, and fold over panel 204. Double perforated score lines 210, 211 and 212 constitute gussets which permit expansion of the retainer in its loaded, closed condition. Needle retainer panel 201 possesses foam block 208 which provides alternate means of needle retention. Suture winding panel 203 possesses triangular extension panel 205 foldable along perforated line 206. Fold over panel 204 and extension panel 217 possess slightly raised ribs 207 and 222, respectively. Raised rib 207 imparts a slight concave bend to fold-over panel 204 which enables panel 204 to resist a tendency to thrust away from needle retainer panel 201. Raised rib 222 functions in a similar manner where extension panel 217 is concerned. Locking tab 213 is defined along double score line 214. When retainer 200 is in the fully closed condition, locking tab 213 folds back along double score line 214 to cooperate with closing slit 215 of panel 202 and provide a completely secured retainer. In the closed position, outer extension panel 217 folds over at double perforated line 218. Tab 221 folds along arcuate perforated line 223 to fit under front cover panel 202 thus providing protection for the secured needle.

The retainers of the invention can be packaged within a foil package of the type described in copending application Ser. No. 388,152, filed Aug. 1, 1989, hereby incorporated by reference, or directly in a so-called "breather pouch" (not shown).

What is claimed is:

1. A suture retainer which comprises
a first panel including means for retaining a needle,
a second single section panel directly connected to the first panel along a common longitudinal edge thereof and including means for at least partially covering one of the other panels,
a third panel connected to the second panel and having means for winding a suture, and
a fourth panel connected to the third panel and including means for folding over upon one of the other panels,
wherein said second panel possesses an upper terminal sloping edge to provide exposure of at least a portion of each needle secured to the first panel in the folded condition of the retainer.

2. A suture retainer which comprises
a first panel including means for retaining a needle,
a second single section panel directly connected to the first panel along a common longitudinal edge thereof and including means for at least partially covering one of the other panels,
a third panel connected to the second panel and having means for winding a suture, and
a fourth panel connected to the third panel and including means for folding over upon one of the other panels,
wherein the first panel possesses means for securing a needle component of at least one combined surgical needle-suture device to an upper region thereof,
the second panel provides exposure of at least a portion of each needle secured to the first panel in the folded condition of the retainer;
the third panel receives the suture component of at least one combined surgical needle-suture device, and
the fourth panel folds over directly upon the second panel in the folded condition of the retainer to provide needle visibility and accessibility from the rear of the retainer.

3. The suture retainer of claim 1 wherein the margin of each of the junctures of the first and second panels, the second and third panels and the third and fourth panels possesses an indentation such that in the folded condition of the retainer, the indentations prevent the suture(s) from becoming caught between the panels when the panels are folded.

4. The suture retainer of claim 1 wherein the first panel possesses a foam block for securing a needle component thereto.

5. The suture retainer of claim 1 wherein the means for securing a needle component to the upper sloping edge of the first panel comprises a cut out associated with or defined upon said edge for accommodating passage of sterilizing gas therethrough.

6. The suture retainer of claim 5 wherein the first panel possesses an extension panel which folds over upon its upper sloping edge to protect each needle component secured thereto.

7. The suture retainer or claim 6 wherein the extension panel possesses at least one serration along its free edge for further securing a needle component thereto.

8. A suture retainer which comprises
a first panel including means for retaining a needle,
a second single section panel directly connected to the first panel along a common longitudinal edge thereof and including means for at least partially covering one of the other panels,
a third panel connected to the second panel and including means for winding a suture, and
a fourth panel connected to the third panel and including means for folding over upon one of the other panels, wherein the third panel possesses an extension panel which folds over upon an exposed needle or exposed needles to provide protection therefor.

9. The suture retainer of claim 8 wherein the extension panel is connected to the third panel by means facilitating its separation therefrom.

10. The suture retainer of claim 8 wherein the extension panel is connected to the third panel by means facilitating folding of said extension panel relative to said third panel so as to provide ready needle visibility.

11. The suture retainer of claim 8 wherein the extension panel possesses convex-shaped sides such that in the folded condition of the retainer, the sides extend outwards from each side of the retainer to provide a profile which facilitates the opening of the retainer.

12. The suture retainer of claim 8 wherein the extension panel possesses a locking tab for securing said extension panel to the fourth panel in the fully closed position.

13. The suture retainer of claim 8 wherein the extension panel possesses a knurled gripping surface.

14. The suture retainer of claim 1 wherein the fourth panel possesses a raised rib projecting outwardly from the reverse side of the fourth panel, such that in the folded condition of the retainer, said rib imparts a concave bend to the fourth panel which counteracts any tendency of the fourth panel to thrust away from the first panel.

15. The suture retainer of claim 1 wherein the third panel possesses a fold-over extension panel for further securing a suture thread to said third panel.

16. The suture retainer of claim 1 wherein the second panel possesses a trapezoidal slit and the fourth panel possesses a locking tab such that in the folded condition of the retainer, said locking tab folds back at a 180° angle upon itself and cooperates with said trapezoidal slit to lock the panels of the retainer together.

17. The suture retainer of claim 1 wherein the second panel possesses an upwardly sloping ridge and the third panel possesses a triangular-shaped extension panel defined along an angled perforated line and ending in a horizontal cut line such that in the folded condition of the retainer said upwardly sloping ridge cooperates with said horizontal cut line to lock the panels together.

18. The suture retainer of claim 1 wherein said third panel possesses an extension which folds over upon an exposed needle or exposed needles to provide protection therefor.

19. The suture retainer of claim 1 wherein said upper sloping edge slopes upwardly from said first panel to said third panel.

20. The suture retainer of claim 1 wherein said fourth panel folds over directly upon said second panel in the folded condition of the retainer.

21. The suture retainer of claim 1 wherein the upper sloping edge slopes upwardly away from the second panel to which the first panel is connected.

22. The suture retainer of claim 4 wherein said arcuate line curves upwardly in a direction away from the second panel to which the first panel is connected.

23. A suture retainer in folded condition, which comprises
 a first panel including means for retaining a needle,
 a second single section panel directly connected to the first panel along a common longitudinal edge thereof and including means for at least partially covering one of the other panels,
 a third panel connected to the second panel and including means for winding a suture, and
 a fourth panel connected to the third panel and including means for folding over upon one of the other panels,
 wherein in said folded condition, the first panel is folded over upon the second panel, the second and first panels are folded over upon the third panel, and the fourth panel is folded over upon the second panel, whereby a portion of each needle retained by the first panel is exposed.

24. The suture retainer of claim 23 wherein the third panel possesses an extension panel which folds over upon an exposed needle or exposed needles to provide protection therefor.

* * * * *

UNITED STATES PATENT AND TRADEMARK OFFICE
CERTIFICATE OF CORRECTION

PATENT NO. : 5,121,836
DATED : June 16, 1992
INVENTOR(S) : Brown et al.

It is certified that error appears in the above-identified patent and that said Letters Patent is hereby corrected as shown below:

Cover page, line [54], "Retainer For Combined Surgical Suture-Needle Device" should read --Retainer For A Combined Surgical Suture-Needle Device--;

Column 1, line 8, after "a" insert --a continuation of commonly assigned, co-pending U.S. patent application Ser. No. 529,222 filed May 25, 1990, now abandoned, which is a--;

Column 1, line 16-17, change "inter alia" to --*inter alia*--;

Column 1, line 26, insert a period after "sutures";

Column 4, line 42, change "!36" to --136--;

Column 6, line 27, change the semi-colon to a comma; and

Column 8, line 4 after "extension" insert --panel--.

Signed and Sealed this

Fourteenth Day of September, 1993

Attest:

BRUCE LEHMAN

Attesting Officer

Commissioner of Patents and Trademarks